(12) United States Patent
Yang et al.

(10) Patent No.: US 8,425,900 B2
(45) Date of Patent: Apr. 23, 2013

(54) METHOD OF DELIVERING A PROTEIN INTO A CELL

(75) Inventors: Yi-Yan Yang, Singapore (SG); Yong Wang, Singapore (SG); Ashlynn Lingzhi Lee, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 377 days.

(21) Appl. No.: 12/598,408

(22) PCT Filed: Apr. 30, 2008

(86) PCT No.: PCT/SG2008/000151
§ 371 (c)(1),
(2), (4) Date: Oct. 30, 2009

(87) PCT Pub. No.: WO2008/133597
PCT Pub. Date: Nov. 6, 2008

(65) Prior Publication Data
US 2010/0119501 A1    May 13, 2010

Related U.S. Application Data

(60) Provisional application No. 60/924,092, filed on Apr. 30, 2007.

(51) Int. Cl.
A61K 38/43     (2006.01)
C12N 9/00      (2006.01)
C12N 9/16      (2006.01)
C12N 5/00      (2006.01)

(52) U.S. Cl.
USPC .......... 424/94.1; 435/183; 435/196; 435/375; 424/94.5

(58) Field of Classification Search .................. None
See application file for complete search history.

(56) References Cited

U.S. PATENT DOCUMENTS

| | | | | |
|---|---|---|---|---|
| 5,824,337 | A * | 10/1998 | Mullen | 424/450 |
| 6,375,975 | B1 * | 4/2002 | Modi | 424/434 |
| 2002/0045263 | A1 * | 4/2002 | Leong et al. | 435/455 |
| 2004/0137071 | A1 * | 7/2004 | Unger | 424/489 |
| 2005/0260276 | A1 * | 11/2005 | Yang et al. | 424/492 |
| 2007/0231412 | A1 | 10/2007 | Hughes et al. | |

FOREIGN PATENT DOCUMENTS

| | | |
|---|---|---|
| EP | 1279682 A2 | 1/2003 |
| EP | 1226212 B1 | 10/2006 |
| JP | 2006273790 A | 10/2006 |
| WO | WO 01/91725 A2 | 12/2001 |
| WO | WO 2005/112886 A2 | 12/2005 |

OTHER PUBLICATIONS

Office Action issued in CN Application No. 200880021216.9 (date of issue Apr. 13, 2011).

English Translation of Office Action issued in CN Application No. 200880021216.9 (date of issue Apr. 13, 2011).

2nd Office Action issued in corresponding Chinese Patent Application No. 200880021216.9 (date of issue—Nov. 16, 2011.

English Translation of 2nd Office Action issued in corresponding Chinese Patent Application No. 200880021216.9 (date of issue—Nov. 16, 2011.

Banga, A.K. And Prausnitz, M.R., "Assessing the potential of skin electroporation for the delivery of protein- and gene-based drugs", Trends in Biotechnology, Oct. 1, 1998, pp. 408-412, vol. 16, Issue 10.

Brustugun, O.T. et al., "Apoptosis induced by microinjection of cytochrome c is caspase-dependent and is inhibited by Bcl-2", Cell Death & Differentiation, Aug. 1998, pp. 660-668, vol. 5, No. 8.

Endo, Y. et al., "The site of action of the A-chain of mistletoe lectin I on eukaryotic ribosomes the RNA N-glycosidase activity of the protein", FEBS Letters, Apr. 25, 1988, pp. 378-380, vol. 231, Issue 2.

Fenton, M. et al., "The efficient and rapid import of a peptide into primary B and T lymphocytes and a lymphoblastoid cell line", Journal of Immunological Methods, 1998, pp. 41-48, vol. 212, Issue 1.

Ford, K.G. et al., "Protein transduction: an alternative to genetic intervention?", Gene Therapy, Jan. 2001, pp. 1-4, vol. 8, No. 1.

Futami, J. et al., "Intracellular delivery of proteins into mammalian living cells by polyehylenimine-cationization", Journal of Bioscience and Bioengineering, Feb. 2005, pp. 95-103, vol. 99, Issue 2.

Kim, M.S. et al., "Activation of caspase cascades in Korean mistletoe (Viscum album var. coloratum) lectin-II-induced apoptosis of human myeloleukemic U937 cells", General Pharmacology, May 2000, pp. 349-355(7), vol. 34, No. 5.

Lee, A.L.Z. et al., "Efficient intracellular delivery of functional proteins using cationic polymer core/shell nanoparticles", Biomaterials, Mar. 2008, pp. 1224-1232, vol. 29, Issue 9.

Lee, H.S. et al., "Isolation and characterization of biologically active lectin from Korean mistletoe, Viscum album var. Coloratum", Cellular and Molecular Life Sciences, Apr. 1999, pp. 679-682, vol. 55, No. 4.

Sakuma, S. et al., "Design of nanoparticles composed of graft copolymers for oral peptide delivery", Advanced Drug Delivery Reviews, Mar. 23, 2001, pp. 21-37, vol. 47, Issue 1.

Vervecken, W. et al., "Induction of apoptosis by mistletoe lectin I and its subunits. No evidence for cytotoxic effects caused by isolated A- and B-chains", The International Journal of Biochemistry & Cell Biology, Mar. 1, 2000, pp. 317-326, vol. 32, Issue 3.

Wadia, J.S. and Dowdy, S.F., "Protein transduction technology", Current Opinion in Biotechnology, Feb. 1, 2002, pp. 52-56, vol. 13, Issue 1.

Wang, Y. et al., "Co-delivery of drugs and DNA from cationic core-shell nanoparticles self-assembled from a biodegradable copolymer", Nature Materials, Oct. 2006, pp. 791-796, vol. 5, Issue 10.

(Continued)

Primary Examiner — Chris R Tate
Assistant Examiner — Douglas F White
(74) Attorney, Agent, or Firm — Klarquist Sparkman LLP

(57) ABSTRACT

There is presently provided a complex of a micelle formed from a cationic polymer and a protein, and a method using the complex to deliver the protein into a cell.

22 Claims, 7 Drawing Sheets

OTHER PUBLICATIONS

Wood, K.C. et al., "A Family of Hierarchically Self-Assembling Linear-Dendritic Hybrid Polymers for Highly Efficient Targeted Gene Delivery", Angewandte Chemie International Edition, Oct. 21, 2005, pp. 6704-6708, vol. 44, Issue 41.

Yoon, T.J. et al., "Lectins isolated from Korean mistletoe (Viscum album coloratum) induce apoptosis in tumor cells", Cancer Letters, Feb. 8, 1999, pp. 33-40, vol. 33, No. 1.

Zelphati, O. et al., "Intracellular Delivery of Proteins with a New Lipid-medicated Delivery System", The Journal of Biological Chemistry, Sep. 14, 2001, pp. 35103-35110, vol. 276, Issue 37.

Supplementary European Search Report dated Oct. 17, 2012 issued in corresponding EP Application No. 08741956.0.

Notice of Reasons for Rejection dated Jan. 7, 2013 issued in corresponding JP Application No. 2010-506144.

* cited by examiner

METHOD OF DELIVERING A PROTEIN INTO A CELL

CROSS-REFERENCE TO RELATED APPLICATION

This application claims benefit of, and priority from, U.S. provisional patent application No. 60/924,092, filed on Apr. 30, 2007, the contents of which are fully incorporated herein by reference.

FIELD OF THE INVENTION

The present invention relates generally to methods of delivering a protein into a cell.

BACKGROUND OF THE INVENTION

Therapeutic approaches to various disorders, diseases and conditions may contemplate the delivery of a biologically active protein into a cell, so that the protein can perform its biological function within a cellular context.

Existing methods for delivery of biologically active proteins into cells include physical methods such as microinjection [6, 7] and electroporation [8, 9], which may prove difficult to apply in vivo.

Molecular techniques include conjugation of a protein transduction domain (PTD) to an active protein for mediation of cellular uptake of the protein. The three most actively studied PTDs are derived from *Drosophilia anntennapedia* peptide, HSV-VP22 protein and the HIV-TAT protein transduction motif. Transduction across cell membranes by these PTDs occurs through a mechanism that presently is not well understood, but studies have shown that the peptide and protein delivery have a strong correlation with the content and distribution of positively charged lysine and arginine residues in the PTDs [10, 11].

Another approach in rational drug delivery research that is becoming increasingly popular involves cationic lipids and polymers. For example, polyethylenimine (PEI)-conjugated proteins are able to enter cells based on ionic charge interactions [12]. The conjugation of proteins with PEI must be conducted under mild conditions to protect proteins from denaturation. Moreover, cytotoxicity of PEI, especially PEI having high molecular weight, also limits its in vivo applications.

There exists a need for alternative approaches for delivering a protein, including a biologically active protein or an antibody, into a cell.

SUMMARY OF THE INVENTION

In one aspect, there is presently provided a micelle-protein complex comprising: a micelle of a cationic polymer, the cationic polymer having a structure of the general formula I—(W—X—Y—Z)$_p$—(WP'—X'—Y'—Z')$_q$—; and a protein, the protein having a region available to complex with the micelle. The protein is complexed to the exterior of the micelle via an interaction between the protein and the cationic polymer.

In the general formula I, each of W, X, Y and Z is independently selected from

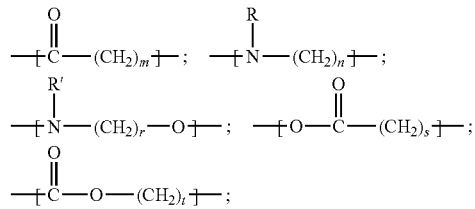

and nothing, wherein only one of W, X, Y and Z is nothing and at least one of W, X, Y and Z is a group containing nitrogen bonded to R or R'.

Also in the general formula I, each of W', X', Y' and Z' is independently selected from

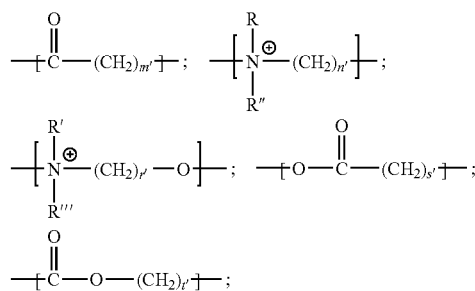

and nothing, wherein only one of W', X', Y' and Z' is nothing, and at least one of W', X', Y' and Z' is a group containing nitrogen bonded to R" or R'".

Also in the general formula I, each of R and R' is independently H, alkyl or heteroalkyl; each of R" and R'" is independently a hydrophobic group; each of p and q is independently an integer greater than zero; and each of m, n, r, s, t, m', n', r', s' and t' is independently an integer greater than 0.

In the presently provided micelle-protein complex, the cationic polymer may comprise poly{N-methyldietheneamine sebacate)-co-[(cholesteryl oxocarbonylamido ethyl)methyl bis(ethylene)ammonium bromide]sebacate}. The protein may be an oligopeptide, a peptide, a polypeptide, a full length protein, a protein fragment, a protein domain, or a fusion protein, and may be biologically active.

In various embodiments, the protein may comprise a hormone, a receptor ligand, a transcription factor, a transcription enhancer, a transcription suppressor, an enzyme, a kinase, a phosphatase, a nuclease, a protease, a growth factor, an antibody, or a cytotoxic protein. In particular embodiments, the growth factor may comprise Glial-derived neurotropic factor, the cytotoxic protein may comprise lectin A and the antibody may comprise herceptin.

The presently provided micelle-protein complex may further comprise an additional therapeutic agent, including a pharmaceutical agent included in the interior of the micelle or a pharmaceutical agent or a nucleic acid molecule complexed to the exterior of the micelle.

In another aspect, there is presently provided a method of delivering a protein into a cell. The method comprises contacting the micelle-protein complex as described herein with a cell so that the micelle-protein complex is taken up into the cell.

The cell may be in vitro, or may be in vivo such that the method comprises administering the micelle-protein complex to a subject, including for example a human.

In certain embodiments the protein is biologically active and retains biological activity after delivery into the cell.

In yet another aspect, there is presently provided a pharmaceutical composition comprising the micelle-protein complex as described herein. The pharmaceutical composition may further comprise a pharmaceutically acceptable carrier.

In still another aspect, there is presently provided use of the micelle-protein complex as described herein for delivering a protein into a cell of a subject. The subject may be a human.

In various embodiments, the protein is biologically active and retains biological activity after delivery into the cell.

Other aspects and features of the present invention will become apparent to those of ordinary skill in the art upon review of the following description of specific embodiments of the invention in conjunction with the accompanying figures.

BRIEF DESCRIPTION OF THE DRAWINGS

In the figures, which illustrate, by way of example only, embodiments of the present invention.

DETAILED DESCRIPTION

Figure 1:
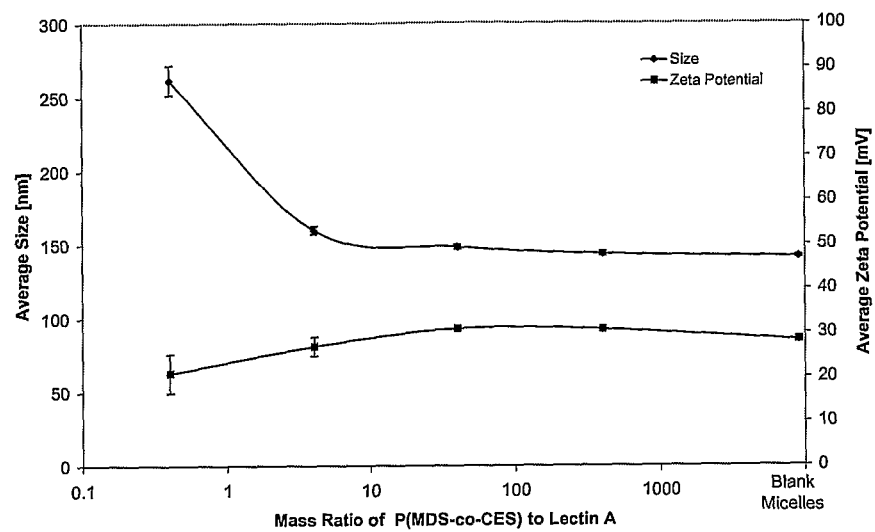
FIG. 1: Particle size and zeta potential of P(MDS-co-CES) micelle/lectin A complexes. Each condition was tested in triplicate. The standard deviation is shown by error bars.

The present methods and compositions relate to the formation of a complex between a biodegradable cationic micelle and a protein, and the use of such complexes to deliver the protein to the interior of a cell.

Novel cationic core-shell micelles were previously described in U.S. patent application Ser. No. 10/849,498 (published as US 2005/0260276). That application relates to the use of biodegradable cationic core-shell micelles for the delivery of pharmaceutical drugs, including drugs encapsulated within the interior of the micelles, and delivery of nucleic acid molecules, including nucleic acid molecules associated with the exterior of the micelles. The polymers that form the micelles are composed of hydrophilic backbone chains with hydrophobic pendant groups attached to the backbone at quaternary amino groups in the backbone. The charged quaternary amino groups provide the polymer with a polycationic nature, with non-neutralizable positive charges distributed along the backbone. The polymers also contain tertiary amino groups along the backbone which can be protonated and deprotonated, allowing for the polymers to have a buffering effect in physiological contexts [14].

As described in US 2005/0260276, pharmaceutical drugs are readily encapsulated within the interior of the micelles by inclusion of a drug with the polymer during assembly of the micelles. Many pharmaceutical drugs contain hydrophobic portions, for example a hydrophobic ring structure, allowing for an association between the drug and the hydrophobic pendant groups on the polymer that tend to segregate to the interior of the micelle structure, although some hydrophobic groups may be located on the exterior of the micelle.

Also described in US 2005/0260276, nucleic acids such as DNA may be readily associated with the exterior of the micelles. Nucleic acids are flexible molecules with negative charges distributed regularly along the molecule backbone and thus can contour to the surface of the micelles and electrostatically associate with the cationic charges at the outer surface of the micelles.

In contrast, proteins may be folded into complex structures, including globular structures, particularly in the case of biologically active proteins where activity is typically dependent on the conformational folding of the protein. Proteins, even when having a region of negative charge, do not tend to have the same charge distribution as polyanionic nucleic acids, and tend not to be able to conform to the surface of the micelle in the same manner as a nucleic acid. As well, proteins tend to be quite sensitive to environment, including microenvironment, and may denature under unfavourable conditions, resulting in a loss of biological activity. Despite these apparent difficulties associated with proteins, the inventors have now determined that the previously described micelles can surprisingly be used to deliver proteins, including folded, biologically active proteins, into a cell.

The core-shell micelles may be used to deliver a protein into the interior of a cell while allowing for retention of biological activity that the protein may possess. Cytotoxic lectin A was used as an exemplary protein having biological activity, and is demonstrated by Example 1 set out below, lectin A was delivered into cells more efficiently than BioPorter, a commercially available protein carrier that comprises a cationic lipid. As well, the cytotoxicity of lectin A against various cancer cell lines was much higher when delivered by the micelles than by BioPorter. Thus, the present methods may result in very efficient delivery of proteins into a cell while maintaining any biological activity the protein may possess. The micelle-protein complex has a variety of applications, including in vitro applications, research, and human medical applications.

Although lectin A was used as an exemplary protein, the present methods and complexes as described herein are intended to extend to proteins in general, including antibodies, for example herceptin; it will be appreciated that the methods and complexes are not dependent on any particular amino acid sequence or biological activity of the protein used in the method or complex.

Thus, there is provided a method for delivering a protein into the interior of a cell. A micelle formed from a biodegradable, cationic, amphilic polymer is used as the delivery vehicle and is used to form a complex with the protein that is to be delivered. The complex is then contacted with the cell to which the protein is to be delivered. The complex is appropriately positively charged and of appropriate dimensions to allow for the complex to be endocytosed and thus be taken into the cell, thereby delivering the protein into the cell.

First, a micelle complexed to a protein is provided. Exemplary micelles, as described in US 2005/0260276, comprise a cationic polymer. As described above, the polymer has a hydrophilic backbone that contains amino groups. The amino groups in the hydrophilic molecule that forms the backbone of the main polymer chain are tertiary amino groups. The tertiary amino groups may be protonated or deprotonated depending on the pH, influencing the net positive charge depending on solution conditions. However, a hydrophobic pendant group is attached to the hydrophilic main chain via at least a portion of the tertiary amino groups, converting such amino groups to perpetually positively charged groups (i.e. quaternary amino groups), resulting in a polymer that is cationic regardless of pH.

The cationic polymer has a structure of general formula I:

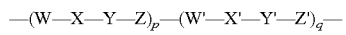

W, X, Y and Z are each independently selected from

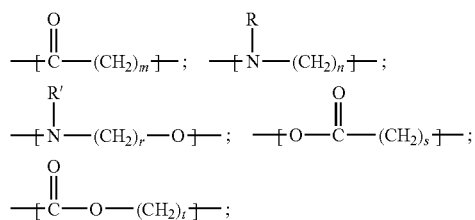

and nothing.

Only one of W, X, Y and Z is nothing and at least one of W, X, Y and Z is a group containing nitrogen bonded to R or R'.

W', X', Y' and Z' are each independently selected from

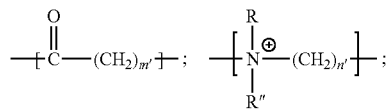

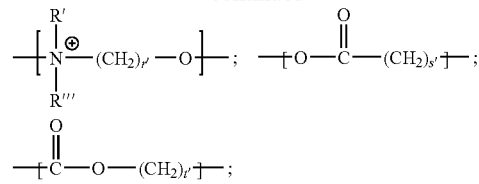

and nothing.

Only one of W', X', Y' and Z' is nothing and at least one of W', X', Y' and Z' is a group containing nitrogen bonded to R'' or R'''.

Each of R and R' is independently H, alkyl or heteroalkyl.

As used herein, alkyl refers to a straight or branched chain saturated hydrocarbon monovalent radical having in the range of 1 to 20 carbon atoms, 1 to 12 carbon atoms or 1 to 8 carbon atoms and is optionally substituted, for example by alkoxy (of an (optionally lower) alkyl group), halogen, trifluoromethyl, cyano, carboxyl, carbamate, sulfonyl, or sulfonamide.

As used herein, heteroalkyl is as defined for alkyl above, but includes one or more heteroatoms (e.g., N, O, S, or the like) as part of the main hydrocarbon chain.

Each of R'' and R''' is independently a hydrophobic group.

As used herein, a hydrophobic group is a monovalent radical formed by removing a hydrogen from a hydrophobic molecule, for example cholesterol, polylactic acid, poly(lactic-co-glycolic) acid, polycaprolactone, polycarbonate or a polyphenol.

Each of p and q is independently a positive integer, for example an integer from 1 to 2000, from 1 to 1000 or from 1 to 500. It will be appreciated that each —(W—X—Y—Z)— and each —(W'—X'—Y'—Z')— monomer may be randomly arranged along the polymer backbone and that the above Formula I does not necessarily imply that the monomers are arranged in blocks.

Each of m, n, r, s, t, m', n', r', s' and t' is independently an integer greater than 0, for example, an integer from 1 to 20, an integer from 1 to 12 or an integer from 1 to 8.

In particular embodiments, the polymer may have a structure of general formula II:

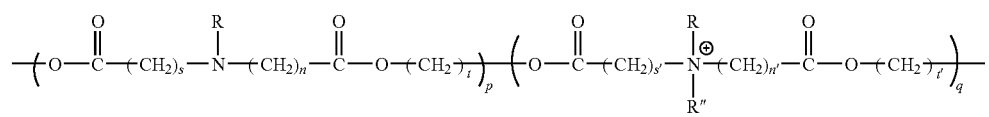

For formula II, each of p, q, n, s, t, n', s', t', R and R'' are as defined above for formula I.

In particular embodiments, the polymer may have a structure of general formula III:

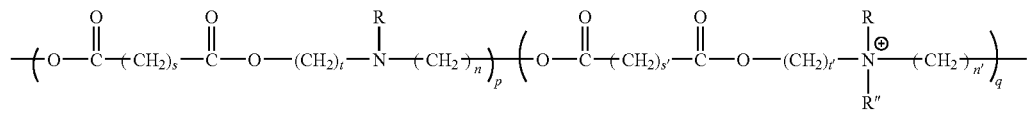

For formula III, each of p, q, n, s, t, n', s', t', R and R" are as defined above for formula I.

In particular embodiments, the polymer may have a structure of general formula IV:

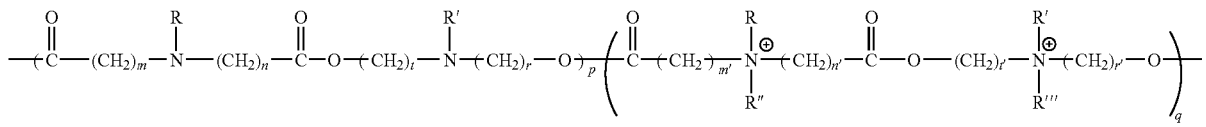

For formula IV, each of p, q, m, n, r, t, m', n', r', t', R, R', R" and R'" are as defined above for formula I.

In a particular embodiment, the polymer comprises poly{N-methyldietheneamine sebacate)-co-[(cholesteryl oxocarbonylamido ethyl)methyl bis(ethylene)ammonium bromide]sebacate} (P(MDS-co-CES)), as described in US 2005/0260276. In a particular embodiment, the polymer is P(MDS-co-CES).

The polymer as described above is biodegradable due to inclusion of the ester and urethano groups along the backbone. As well, the polymer is amphiphilic due to the ester, ether and amino groups located along the backbone and the hydrophobic groups grafted onto the backbone at amino groups along the backbone. The amphiphilic nature of the polymer allows the polymer to form micelles, with the hydrophobic groups tending to be located toward the interior of the micelle and the hydrophilic cationic backbone tending to be located toward the exterior of the micelle when formed in aqueous or hydrophilic solution.

The degree of substitution of the backbone with the grafted hydrophobic group influences the total net charge and positive charge distribution of the polymer by the formation of positively charged quaternary substituted amino groups, as can be seen in Formulae I-IV. The backbone is thus substituted with the grafted hydrophobic group to a degree sufficient to allow the polymer to form micelles and to provide an appropriate cationic charge to the polymer in order to allow for the micelle to complex with a protein to deliver the protein into a cell. The degree of substitution may be, for example, from about 1% to about 100%, from about 10% to about 90%, from about 20% to about 50%, from about 25% to about 40%. Alternatively, the degree of substitution may be less than about 100%, less than about 90%, less than about 80%, less than about 50%, less than about 40%, less than about 30%, less than about 20%, greater than about 25%, greater than about 30%, greater than about 40%, greater than about 50%, greater than about 80%, greater than about 90%. The percentages given for degree of substitution are measured as (the number of quaternary amino groups on the backbone that include a hydrophobic group substituent) divided by (the number of possible amino groups available for substitution with a hydrophobic group) multiplied by 100%.

The polymer chain length has a weight average molecular weight sufficient to allow the polymer to form into a micelle, including by self-assembly. In various embodiments, the polymer has a weight average molecular weight of from about 1 kDa to about 50 kDa, from about 1 kDa to about 30 kDa, from about 5 kDa to about 30 kDa, from about 5 kDa to about 20 kDa, from about 5 kDa to about 15 kDa, from about 8 kDa to about 12 kDa or from about 3 kDa to about 8 kDa.

The polymer may be prepared by standard chemistry techniques known in the art, including those described in US 2005/0260276 and those set out in the Example described below. For example, suitable condensation reactions may be used to react appropriate monomers to obtain the desired hydrophilic backbone. The backbone may then be reacted with an appropriate hydrophobic molecule to undergo a reaction between a nitrogen atom of a tertiary amino group on the polymer backbone and an electron-poor centre in the hydrophobic molecule.

Specifically, a synthesis mechanism for P(MDS-co-CES) is described in US 2005/0260276, in Wang, et al. *Nat. Mater.* 2006, 5, 791 and in the Example 1 described below.

The cationic polymer may thus be assembled into a micelle. The micelle may be formed using standard methods known in the art and as described in US 2005/0260276. For example, micelles may generally be formed by dissolution techniques, dialysis techniques or by single emulsion techniques as are known in the art.

The cationic polymer may be designed so as to self-assemble into micelles, including by using dialysis techniques in which the cationic polymer is dissolved in a suitable solvent such as a polar aprotic solvent (e.g. dimethylformamide) and then dialysed against water or an aqueous buffer solution, including as described in US 2005/0260276 and in the Example set out below.

The micelle size is such that the micelle, when complexed with a protein, may be of sufficient size to allow for endocytosis of the micelle-protein complex by a cell to which the protein is to be delivered. For example, the micelle may be of a cross-sectional size of less than about 1 μm, about 250 nm or less, about 180 nm or less, from about 10 nm to about 250 nm, from about 50 nm to about 200, from about 100 nm to about 200 nm, from about 100 nm to about 180 nm, from about 130 nm to about 160 nm, about 150 nm.

In the presently described methods, the micelle is complexed with a protein. References herein to a "micelle-protein complex" or references herein that the protein and micelle "are complexed" or form a "complex" refer to an interaction between the micelle and protein that is sufficiently stable to allow for the protein to associate with the micelle in order to be delivered into a cell. References herein to "delivery into" a cell, or "delivered into" a cell means that the protein enters into the interior of the cell from the exterior of the cell, becoming localised in the cytosol or within an organelle of the cell.

As used herein, protein refers to two or more amino acids linked together into a chain via peptide (amide) linkages, and includes a polypeptide, an antibody, a full length protein, a protein fragment, a protein domain, or a fusion protein. A polypeptide may be an oligopeptide or a peptide.

The protein may be biologically active in that it possesses a biological function in certain biological contexts, such as enzyme activity, binding to a target molecule such as another protein or protein domain or a nucleic acid sequence, hormone activity, cell signalling activity, transcription activation or suppression activity, cell growth or cell cycle regulation, anti-cancer activity or cytotoxic activity.

The protein will have a region or portion of the protein that is available to form a complex with the micelle. For example, the protein may form a complex with the micelle via a hydrophobic, electrostatic or hydrogen bonding interaction between various functional groups available on the protein and complementary functional groups available on the exterior of the micelle.

Thus, in order to complex the micelle with the protein that is to be delivered into the cell, the protein may have a negatively charged, or anionic, region such as a portion of the protein or a tag attached to the protein. The negative charges on the protein allow the protein to form a complex with the cationic micelle via electrostatic interaction. For example, if the protein is a short oligopeptide, the oligopeptide may contain one or more negatively charged amino acids along its length, such as aspartic acid or glutamic acid. If the protein is a folded chain, including a full-length protein, an antibody, a protein domain or a fusion protein, the protein may contain a region on the surface of the protein that is negatively charged due to the spatial arrangement of negatively charged amino acids at the surface of the protein. The protein may be designed as a fusion protein having a stretch of amino acids containing negatively charged amino acids, for example at the C-terminus of a biologically active protein or protein domain. Alternatively, the protein may be modified with a negatively charged group or tag attached to the protein. It will be appreciated that any modification, including by fusion of additional amino acids or by attachment of a negatively charged tag, should be done so as not to interfere with the biological function of the protein.

Alternatively, in order to complex the micelle with the protein that is to be delivered into the cell, the protein may have a hydrophobic region such as a portion of the protein or a tag attached to the protein. The hydrophobic region of the protein allows the protein to form a complex with the cationic micelle via hydrophobic interaction with any hydrophobic pendant groups exposed on the exterior of the micelle. For example, if the protein is a short oligopeptide, the oligopeptide may contain one or more hydrophobic amino acids along its length, for example phenylalanine, tryptophan, isoleucine, leucine or valine. If the protein is a folded chain, including a full-length protein, an antibody, a protein domain or a fusion protein, the protein may contain a region on the surface of the protein that is hydrophobic due to the spatial arrangement of hydrophobic amino acids at the surface of the protein. The protein may be designed as a fusion protein having a stretch of amino acids containing hydrophobic amino acids, for example at the C-terminus of a biologically active protein or protein domain. Alternatively, the protein may be modified with a hydrophobic group or tag attached to the protein. It will be appreciated that any modification, including by fusion of additional amino acids or by attachment of a hydrophobic tag, should be done so as not to interfere with the biological function of the protein.

Alternatively, in order to complex the micelle with the protein that is to be delivered into the cell, the protein may have a polar or charged region such as a portion of the protein or a tag attached to the protein. The polar or charged groups on the protein allow the protein to form a complex with the cationic micelle via hydrogen bonding interactions. For example, if the protein is a short oligopeptide, the oligopeptide may contain one or more polar or charged amino acids along its length that contain functional groups capable of acting as hydrogen bond donor or acceptor groups, such as for example tyrosine, serine, threonine, arginine, glutamine or lysine. If the protein is a folded chain, including a full-length protein, an antibody, a protein domain or a fusion protein, the protein may contain a region on the surface of the protein that is polar or charged due to the spatial arrangement of polar or charged amino acids at the surface of the protein. The protein may be designed as a fusion protein having a stretch of amino acids containing polar or charged amino acids, for example at the C-terminus of a biologically active protein or protein domain. Alternatively, the protein may be modified with a polar or charged group or tag attached to the protein that contains functional groups capable of acting as a hydrogen bond donor or acceptor group. It will be appreciated that any modification, including by fusion of additional amino acids or by attachment of a polar or charged tag, should be done so as not to interfere with the biological function of the protein.

Particular proteins that may be complexed with the micelle for delivery to a cell may comprise or be a hormone, a receptor ligand, a transcription factor, a transcription enhancer, a transcription suppressor, an enzyme, a kinase, a phosphatase, a nuclease, a protease, a growth factor, for example Glial-derived neurotropic factor, a cytotoxic protein, for example lectin A, or an antibody, for example herceptin.

If desired, the micelle may be used to deliver an additional therapeutic agent into a cell along with the protein. For example, a pharmaceutical agent such as a drug may be included in the interior of the micelle during formation of the micelle, as described in US 2005/0260276. Alternatively, if the pharmaceutical agent possesses sufficient negative charge, polar hydrogen bond donor or acceptor groups or hydrophobic domains, the pharmaceutical agent may be complexed with the exterior of the micelle in the same manner as the protein. A nucleic acid and a protein may be both complexed with the exterior of the micelle, which may allow for specific targeting and/or synergistic therapeutic effect in the cell.

Thus, the micelle is complexed with a protein that is to be delivered into a cell, and optionally an additional therapeutic agent, including a small molecule drug or a nucleic acid. The micelle may be complexed by addition of the micelle to a solution containing the protein and optional additional therapeutic agent (if to be complexed with the exterior of the micelle).

The ratio of the mass of protein to mass of the micelle may be optimized to ensure adequate formation of the complex and to provide a complex having the desired size and zeta potential, using routine laboratory methods. In certain embodiments, a mass ratio of micelle:protein of about 0.2 or greater, or about 1 or greater, or about 2.5 or greater, or about 5 or greater, or about 10 or greater, or about 20 or greater, or about 30 or greater, or about 40 or greater, or about 50 or greater, allows for efficient, stable complex formation. Zeta potential, a measure of surface charge, may be used as a parameter to gauge complex formation. For example, a positive zeta potential, for example of about 5 mV or greater, from about 5 mV to about 20 mV, or from about 20 mV to about 100 mV may be used to indicate formation of an appropriate complex between the protein and the micelle.

Once a micelle complexed to a protein is provided (including any optional additional therapeutic agent), the complex may be delivered to a cell to allow for uptake of the protein into the cell.

Delivery to a cell comprises contacting the micelle-protein complex with the surface of a cell. Without being limited to any particular theory, the micelle-protein may be endocytosed by the cell, resulting in uptake of the micelle-protein complex into the cell. Once inside the cell, the complex may dissociate, releasing the protein into a cellular compartment, such as an endosome. In the endosome, at least some of the tertiary amino groups in the polymer may become protonated, causing the breakdown of the endosomal membrane and allowing the complex to escape from the endosome, thus releasing the protein into the cytosol.

The cell to which the protein is to be delivered may be any cell, including an in vitro cell, a cell in culture, or an in vivo cell within a subject. The term "cell" as used herein refers to and includes a single cell, a plurality of cells or a population of cells where context permits, unless otherwise specified. The cell may be an in vitro cell including a cell explanted from a subject or it may be an in vivo cell in a subject. Similarly, reference to "cells" also includes reference to a single cell where context permits, unless otherwise specified.

The cell may be derived from any organism, for example an insect, a microorganism including a bacterium, or an animal including a mammal including a human.

When delivered into the cell, the protein may retain its biological function, if any, as described above. A skilled person can readily determine whether the protein has been delivered into the cell using known methods and techniques, including protein detection methods, immunoassays and fluorescence labelling techniques. A skilled person can also readily determine whether the protein retains its biological function provided there exists a direct or indirect assay for that particular biological function within the cell. For example, if kinase activity is to be detected, phosphorylation levels of a target protein may be compared before and after delivery of the protein, including using radiolabelled phosphate.

There is also provided a micelle-protein complex as described above, including a micelle-protein complex containing an additional therapeutic agent.

There is also provided use of the above-described micelle-protein complex for delivering the protein into a cell, or use of the above-described micelle-protein complex for the manufacture of a medicament for delivering the protein into a cell, including when the cell in an in vivo cell in a subject.

To aid in administration of such a micelle-protein complex to a subject, the complex may be formulated as an ingredient in a pharmaceutical composition.

Therefore, there is provided a pharmaceutical composition comprising a micelle-protein complex as described above. The pharmaceutical composition may further include a pharmaceutically acceptable diluent or carrier. The pharmaceutical composition may routinely contain pharmaceutically acceptable concentration of salts, buffering agents, preservatives and various compatible carriers. For all forms of delivery, the micelle-protein complex may be formulated in a physiological salt solution.

The proportion and identity of the pharmaceutically acceptable diluent or carrier is determined by the chosen route of administration, compatibility with biologically active proteins if appropriate, and standard pharmaceutical practice.

The pharmaceutical composition can be prepared by known methods for the preparation of pharmaceutically acceptable compositions suitable for administration to subjects, such that an effective amount of the micelle-protein complex and any additional active substance or substances is combined in a mixture with a pharmaceutically acceptable vehicle. An effective amount of micelle-protein complex is administered to the subject. The term "effective amount" as used herein means an amount effective, at dosages and for periods of time necessary to achieve the desired result, for example to deliver the protein into the target cell or cell population within the subject.

Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the micelle-protein complex, in association with one or more pharmaceutically acceptable vehicles or diluents, and contained in buffer solutions with a suitable pH and iso-osmotic with physiological fluids.

Under ordinary conditions of storage and use, such pharmaceutical compositions may contain a preservative to prevent the growth of microorganisms, and that will maintain any biological activity of the protein. A person skilled in the art would know how to prepare suitable formulations. Conventional procedures and ingredients for the selection and preparation of suitable formulations are described, for example, in Remington's Pharmaceutical Sciences and in The United States Pharmacopeia: The National Formulary (USP 24 NF19) published in 1999. Alternatively, the complex may be formulated at a time sufficiently close to use by mixing the micelle and protein solutions, without the need for preservatives.

When administered to a patient, the micelle-protein complex is administered in an amount effective and at the dosages and for sufficient time period to achieve a desired result. For example, the micelle-protein complex may be administered in quantities and dosages necessary to deliver a protein which may function to alleviate, improve, mitigate, ameliorate, stabilize, prevent the spread of, slow or delay the progression of or cure an infection, disease or disorder, or for example to inhibit, reduce or impair the activity of a disease-related enzyme. A disease-related enzyme is an enzyme involved in a metabolic or biochemical pathway, which when the pathway is interrupted, or when regulatory control of the enzyme or pathway is interrupted or inhibited, the activity of the enzyme is involved in the onset or progression of a disease or disorder.

The effective amount of micelle-protein complex to be administered to a subject can vary depending on many factors such as the pharmacodynamic properties of the micelle-protein complex, the mode of administration, the age, health and weight of the subject, the nature and extent of the disorder or disease state, the frequency of the treatment and the type of concurrent treatment, if any, and the concentration and form of the micelle-protein complex.

One of skill in the art can determine the appropriate amount based on the above factors. The conjugate may be administered initially in a suitable amount that may be adjusted as required, depending on the clinical response of the subject. The effective amount of micelle-protein complex can be determined empirically and depends on the maximal amount of the micelle-protein complex that can be administered safely. However, the amount of micelle-protein complex administered should be the minimal amount that produces the desired result.

The pharmaceutical composition may be administered to a subject in a variety of forms depending on the selected route of administration, as will be understood by those skilled in the art. Non-oral routes are preferred, particularly if a bioactive agent is being administered simultaneously in the same form with the micelle-protein complex. The composition of the invention may be administered surgically or by injection to the desired site. In different embodiments, the composition is administered by injection (parenterally, subcutaneously, intravenously, intramuscularly, by direct injection into a targeted tissue or organ etc.) directly at a desired site.

The present methods and uses are further exemplified by way of the following non-limited examples.

EXAMPLES

Example 1

In this example, lectin A was used as an exemplary anionic biologically active protein to be delivered into a cell. For several decades, research has been focused on lectins from extracts of mistletoe as therapeutically active substances for human cancer. Many studies have described the ability of potent and cytotoxic Korean mistletoe to induce apoptosis in several in vitro systems. Cytotoxic lectins isolated from, an extract of the Korean mistletoe (*Viscum album* var. *Coloratum*) are glycoproteins that induce apoptosis in tumour cells [1]. Reports have shown that Korean mistletoe lectin-II (ML-II) is cytotoxic to Molt4 cells [2, 3], and is able to bring about apoptotic death of U937 cells via activation of caspase cascades [4].

Anticancer activities relating to this species of *V. album* is due to lectin A, which belongs to the type 2 ribosome inactivating proteins (RIP II), consisting of two disulfide-linked protein subunits [1, 3]. The catalytically active A-chain with rRNA N-glycosidase activity inactivates the ribosome by causing the depurination of adenine at position 4324 in the 28S rRNA [5]. This leads to the disruption of the translocation steps of cellular translation during protein biosynthesis and in turn, cell death occurs.

The counterpart of lectin A, the B-chain, does not possess direct cytotoxic property but serves to mediate the transport and targeting of the cytotoxic A-chain by binding to the glycoprotein on cell surface with suitable carbohydrate residues. Lectin B also plays an important role in facilitating the subsequent internalization of the A-chain via endocytosis as lectin A is only be able to elicit its cytotoxic effects after it has been imported into cells [3].

The isolation of ML II from plant extract or its production via recombinant methods encompasses difficulties such as extensive purification and scale-up problems. Hence, the present example provides an alternative stable and competent carrier for intracellular delivery of lectin A.

Materials and Methods

Materials: Recombinant lectin A (Mw: 30.7 kDa) was produced in Ho Sup Yoon's laboratory in Nanyang Technological University, Singapore. P(MDS-co-CES) was synthesized according to the protocols reported previously [13]. Dimethyl sulfoxide (DMSO) and dimethyl formamide (DMF) were purchased from Sigma-Alrich, USA. Dialysis buffer used for micelles fabrication was self-prepared using sodium acetate and acetic acid of ACS grade from Merck, USA. Unless stated otherwise, all reagents and solvents were of commercial grade, and were used as received. MDA-MB-231, HeLa, HepG2 and 4T1 cell lines were obtained from ATCC, USA, and cultured according to ATCC's recommendation. HepG2 and HeLa were grown in DMEM, MDA-MB-231 in Leibovitz L-15 and 4T1 in RPMI 1640. All the media were supplemented with 10% fetal calf serum, 100 U/ml penicillin and 100 μg/ml streptomycin (HyClone, USA). BioPorter™ was purchased from Genlantis, USA, and used according to the manufacturer's instructions. 3-[4,5-Dimethylthiazol-2-yl]-2,5-diphenyl tetrazolium bromide (MTT) was obtained from Sigma, USA, which was used in phosphate-buffered saline (PBS, pH7.4) with a concentration of 5 mg/ml, and the solution was filtered with a 0.22 μm filter to remove blue formazan crystals.

Preparation and characterization of P(MDS-co-CES) micelles: P(MDS-co-CES) was obtained by a three-step synthesis [13]. First, the main chain, poly(N-methyldietheneamine sebacate) (PMDS), was produced by condensation polymerization between N-methyldiethanolamine and sebacoyl chloride. Excess triethylamine was used to remove hydrochloride and limit protonation of the tertiary amine. Next, cholesteryl chloroformate was allowed to react with 2-bromoethylamine hydrobromide in an amidation reaction. The resulting hydrophobic N-(2-bromoethyl)carbarmoyl cholesterol was then grafted onto the hydrophilic poly(N-methyldietheneamine sebacate) main chain through a quaternization reaction to obtain the final product. The main chain was a polyester, and the pendant chain contained potentially hydrolytically labile urethano groups, rendering this copolymer degradable. The degree of cholesterol grafting was about 28.5%. P(MDS-co-CES) had a weight average molecular weight ($M_w$) of ~5.0 kDa with a polydispersity index of 1.7, as measured by gel permeation chromatography. To prepare the cationic micelles, 15.0 mg of P(MDS-co-CES) was dissolved in 5.0 ml of DMF, which was placed in a dialysis membrane with a molecular weight cut-off of 2000 Da (Spectrum Laboratories, USA). The dialysis bag was then immersed in 500 ml of 20 mM sodium acetate/acetic acid buffer with pH 4.6 at room temperature for 24 hours. The dialysis buffer was replaced hourly with fresh buffer solution for the first 8 hours during the 24 hour course. At the end of the dialysis process, the resulting micelle solution was then filtered through a 0.22 μm filter in sterile environment to remove large aggregates. The micelles were characterized with respect to their size and zeta potential using a zetasizer with dynamic light scattering capability (scattering angle: 90°) and equipped with a He—Ne laser beam at 658 nm (Malvern Instruments Zetasizer Nano ZS, UK). Each measurement was repeated in triplicates and the average values were presented.

Micelle/lectin A complex formation: Recombinant lectin A used in this study was kept in an ice bath during the experiments to prevent disruption to its structural stability caused by temperature changes. Lectin A was first added to sodium acetate/acetic acid buffer at pH 6.0. Micelle/lectin A complexes were then formed by adding the freshly prepared micelle solution to the protein solution in varying mass ratios, and mixed gently. The complex solution was left to stand at room temperature for 30 minutes before being characterized and introduced into the cancer cells.

Cytotoxicity study: HepG2, HeLa, MDA-MB-231 and 4T1 cancer cells were seeded onto 96-well plates at a density of $1\times10^4$ cells per well, and cultivated in 100 μl of growth medium. The plates were then returned to incubators for 24 hours to reach 70%-80% confluency before the administration of micelle/lectin A complexes. When the desired cell confluency was reached, the spent growth medium was removed from each well and replaced with 100 μl of the pre-prepared complex solution. After 4 hours of incubation with the complexes, the medium was replaced with fresh one. The plates were then returned to the incubator and maintained in 5% $CO_2$, at 37° C., for 2 days. Each condition was tested in eight replicates. At the end of the 2 days incubation, the culture medium was replaced with 100 μl of fresh medium plus 20 μl of MTT solution. The plates were then returned to the incubator and maintained in 5% $CO_2$, at 37° C., for a further 3 hours. The growth medium and excess MTT in each well were then removed. 200 μl of DMSO was then added to each well to dissolve the internalised purple formazan crystals. An aliquot of 100 μl was taken from each well and transferred to a new 96-well plate. The plates were then assayed at 550 nm and reference wavelength of 690 nm using a microplate reader (PowerWave X, Bio-tek Instruments, USA). The absorbance readings of the formazan crystals were taken to be those at 550 nm subtracted by those at 690 nm. The results were expressed as a percentage of the absorbance of the blank.

Results and Discussion

Characterization of micelles and micelle/lectin A complexes: As shown in FIG. 1, blank P(MDS-co-CES) micelles had an average size of 140 nm and zeta potential of about 28 mV. At low micelles to lectin A mass ratios of 5 or below, the amount of polymer was insufficient to fully condense and bind lectin A, and the size of the particles might be too large for endocytotic uptake (>160 nm). At mass ratios above 5, the size of the complexes remained relatively similar at approximately 150 nm while the zeta potential was between 25 to 30 mV, indicating that at these mass ratios, lectin A was well condensed and complexed with the micelles. The small size and positive zeta potential of the complexes rendered them to be suitable for endocytotic cellular uptake.

Figure 2:
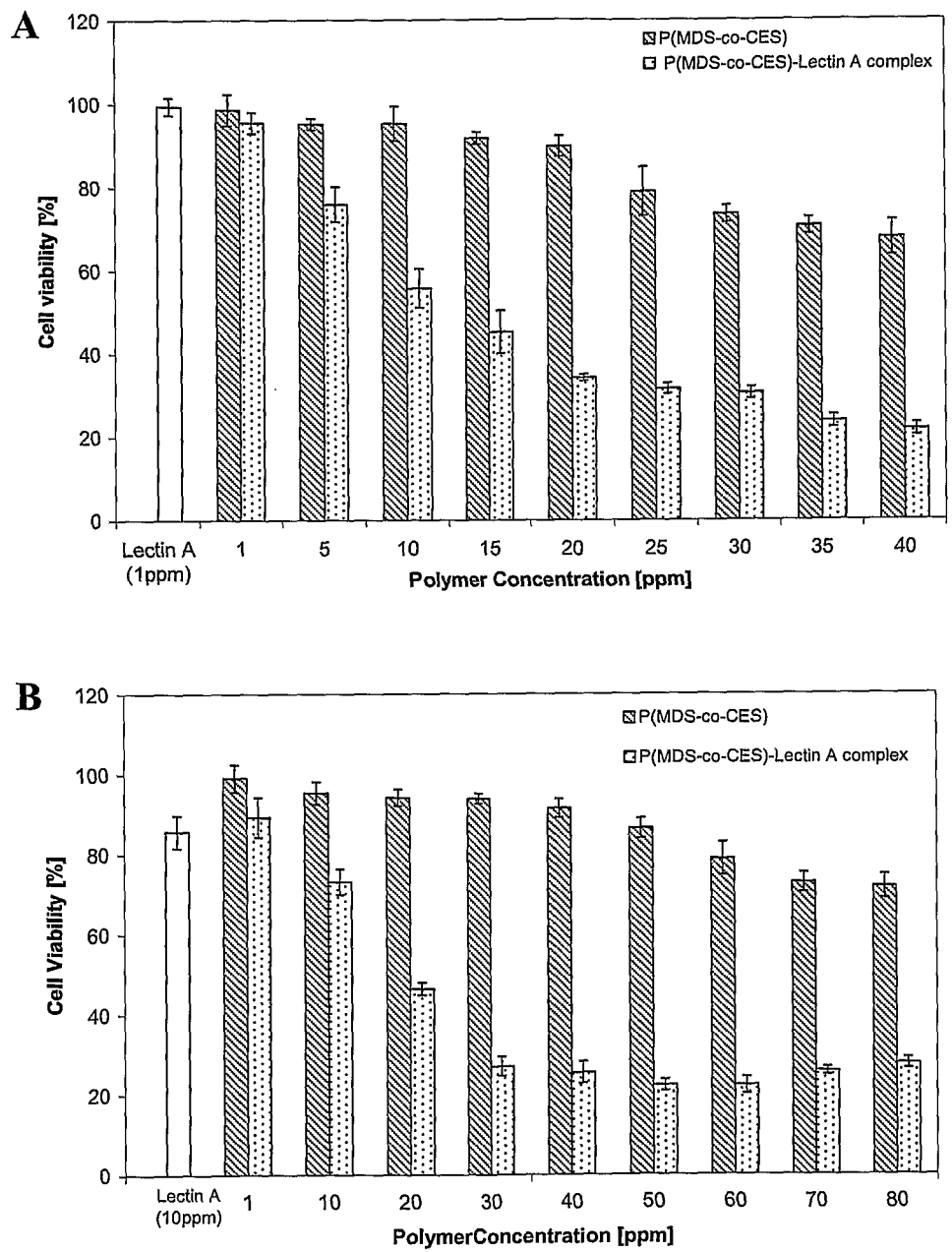
FIG. 2: Viability of MDA-MB-231 (a), HepG2 (b), HeLa (c) and 4T1 (d) cells after being incubated with micelle/lectin A complexes containing a fixed concentration of lectin A and P(MDS-co-CES) of varying concentration. Each condition was tested in eight replicates. The standard deviation is shown by error bars.
Figure 2:
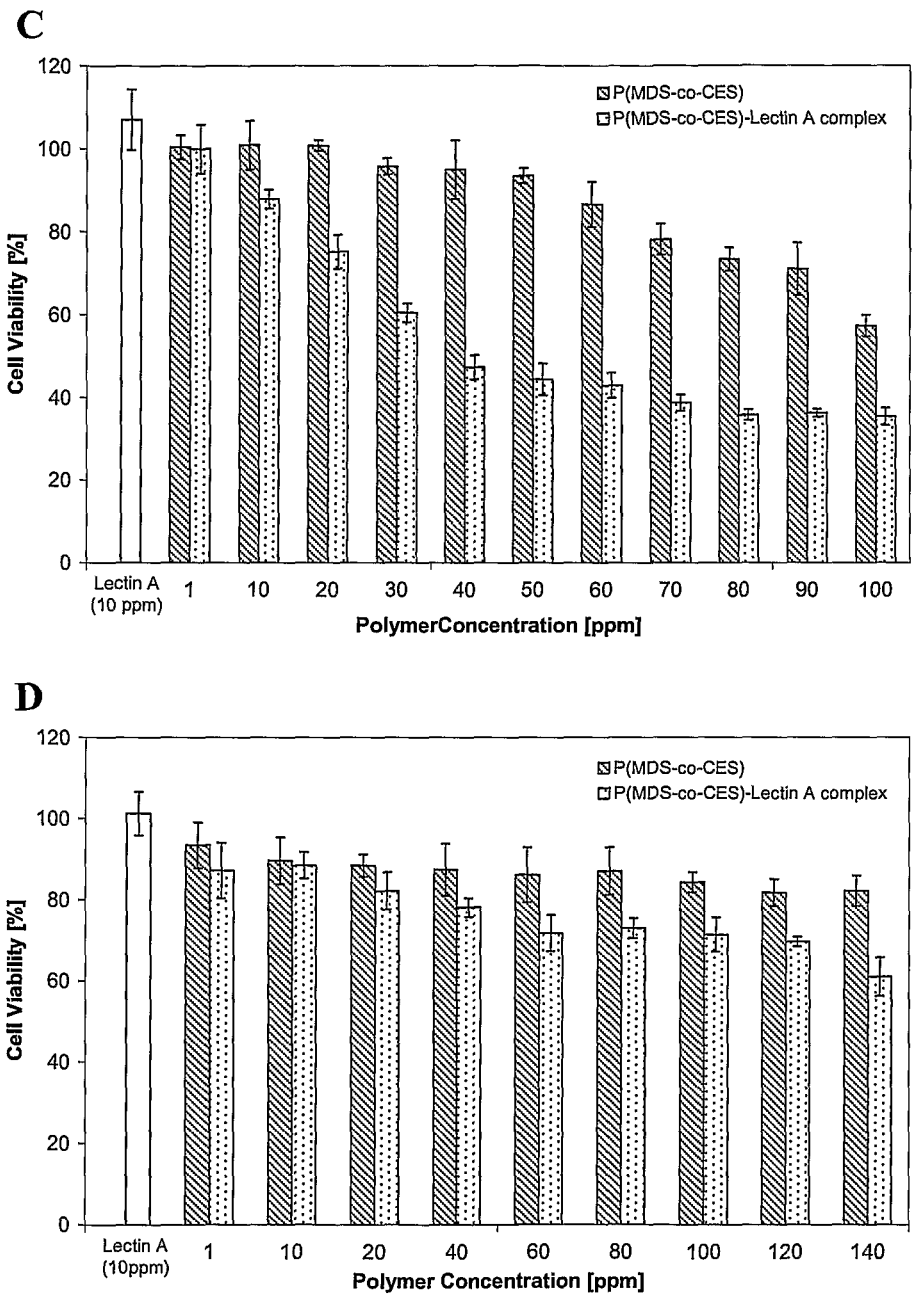

Cytotoxicity of lectin A, micelles and micelle/lectin A complexes: Cytotoxic effects of lectin A, micelles and micelle/lectin A complexes were evaluated against MDA-MB-231, HeLa, HepG2 and 4T1 cells. The blank micelles possessed non-selective cytotoxicity, which increased with increasing doses. Therefore, polymer concentration was first optimized to minimize its cytotoxic effects, while at the same time, to provide a sufficient amount for lectin A to be efficiently delivered. FIG. 2 shows the effect of polymer concentration on cytotoxicity of lectin A at a fixed concentration of lectin A. It is observed that blank P(MDS-co-CES) micelles did not have significant cytotoxicity against all four cell lines at low concentrations. It did give rise to cytotoxicity especially against MDA-MB-231, HepG2 and HeLa cells at high concentrations. In addition, pure lectin A did not exert significant cytotoxicity on cells, indicating that lectin A was unable to enter the cells and elicit its cytotoxic properties without a transport carrier. In sharp contrast, when P(MDS-co-CES) micelles were used to deliver lectin A, the cancer cells were successfully eliminated. With an appropriate amount of polymer used to deliver lectin A, percentage of viable cells left after treatment was significantly reduced for all four cell lines.

From FIG. 2, it can also be observed that for all the cell lines tested, the cytotoxic effect of lectin A was insignificant at low polymer concentrations possibly because lectin A was not well condensed and the micelle/lectin A complexes were of too large size for efficient cellular uptake. On the other hand, blank P(MDS-co-CES) micelles exerted non-selective cytotoxicity especially at high concentrations. Hence, it is necessary to identify the optimal polymer concentration. For MDA-MB-231, the optimum P(MDS-co-CES) concentration was identified to be 20 ppm. The reason behind this is that as the polymer concentration increased beyond 20 ppm with the fixed lectin A concentration of 1 ppm, the cell viability remained relatively constant at 22-34%. However, the cell viability increased continuously when polymer concentration decreased from 20 to 1 ppm. More importantly, the polymer did not show significant cytotoxicity at 20 ppm. By applying similar principles to the other three cell lines, the optimum polymer concentrations were analyzed to be 50, 40 and 100 ppm for HeLa, HepG2 and 4T1 respectively.

Figure 3:
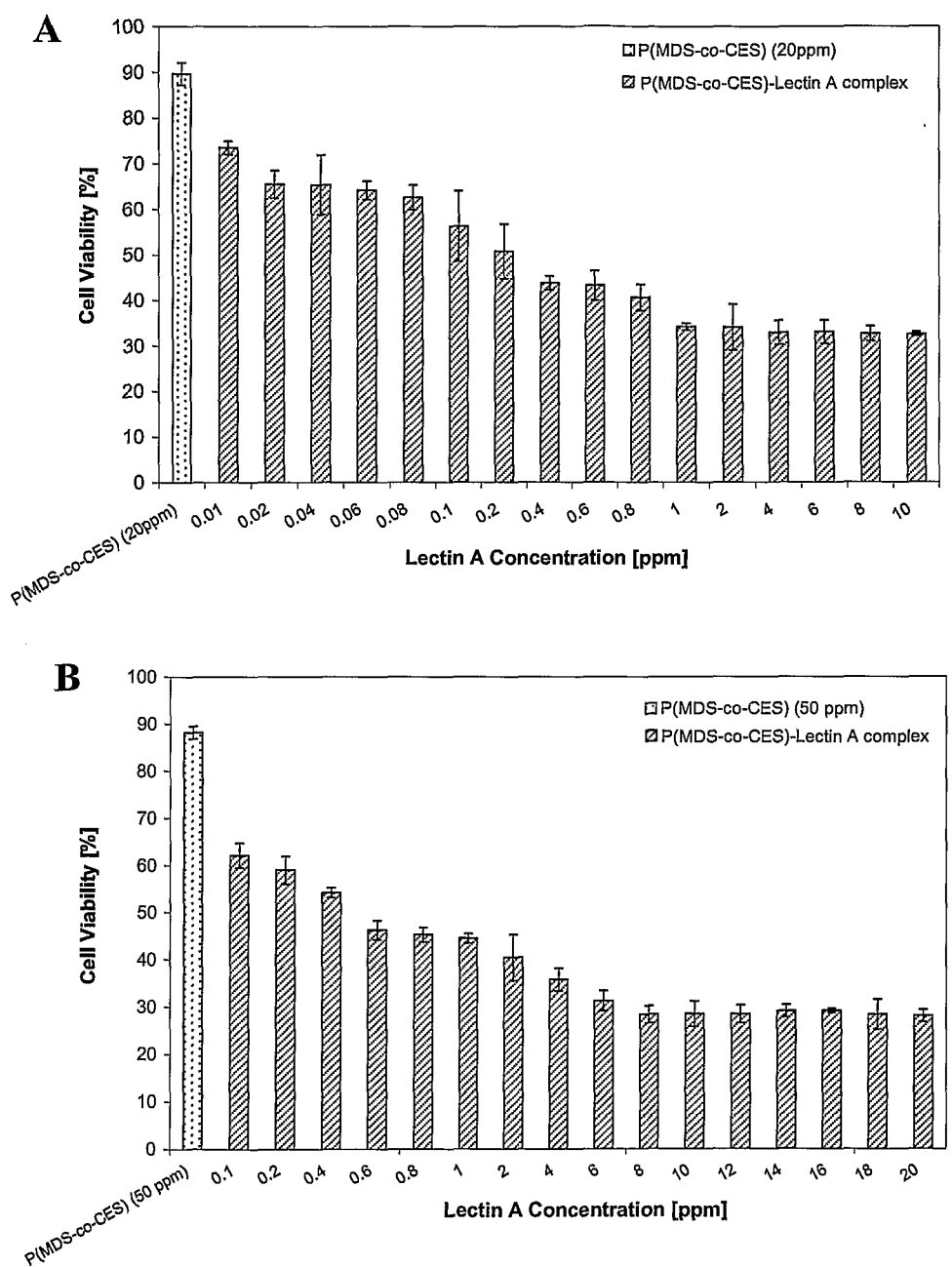
FIG. 3: Viability of MDA-MB-231 (a), HepG2 (b), HeLa (c) and 4T1 (d) cells after being incubated with micelle/lectin A complexes containing a varying concentration of lectin A and a fixed concentration of P(MDS-co-CES). Each condition was tested in eight replicates. The standard deviation is shown by error bars.
Figure 3:
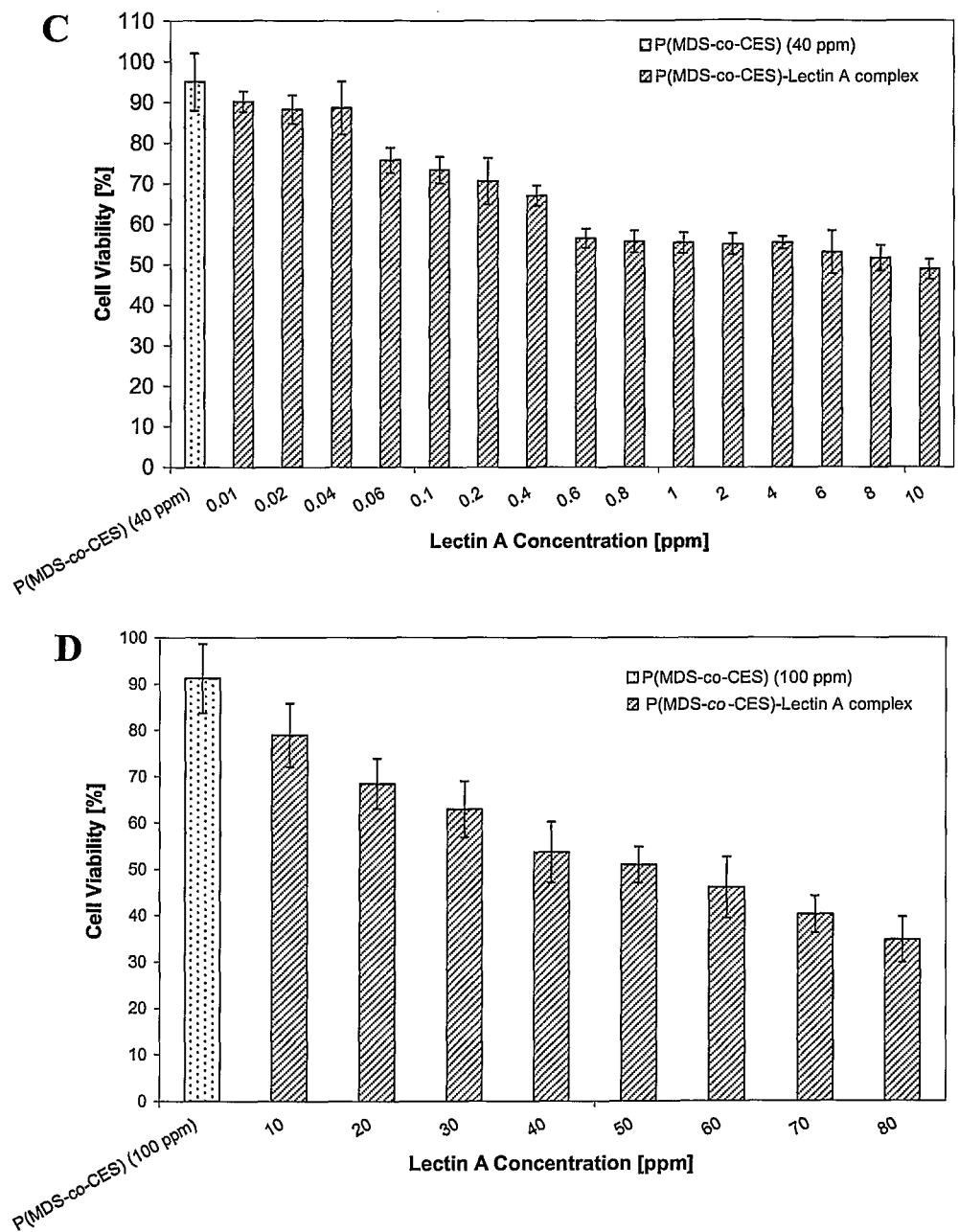

With the optimum polymer concentration identified and fixed, studies were carried out subsequently to determine the $IC_{50}$ value of lectin A. FIG. 3 shows cell viability at varying lectin A concentration, from which the $IC_{50}$ values of lectin A were determined to be 0.2, 0.5, 10 and 50 ppm for MDA-MB-231, HeLa, HepG2 and 4T1 cells respectively. Differences in $IC_{50}$ between the various cell lines revealed their different degrees of sensitivity to the cytotoxicity of micell/lectin A complexes. MDA-MB-231 cells showed the least tolerance to the cytotoxic effects of the complexes, followed by HeLa, HepG2 and 4T1 cells.

Figure 4:
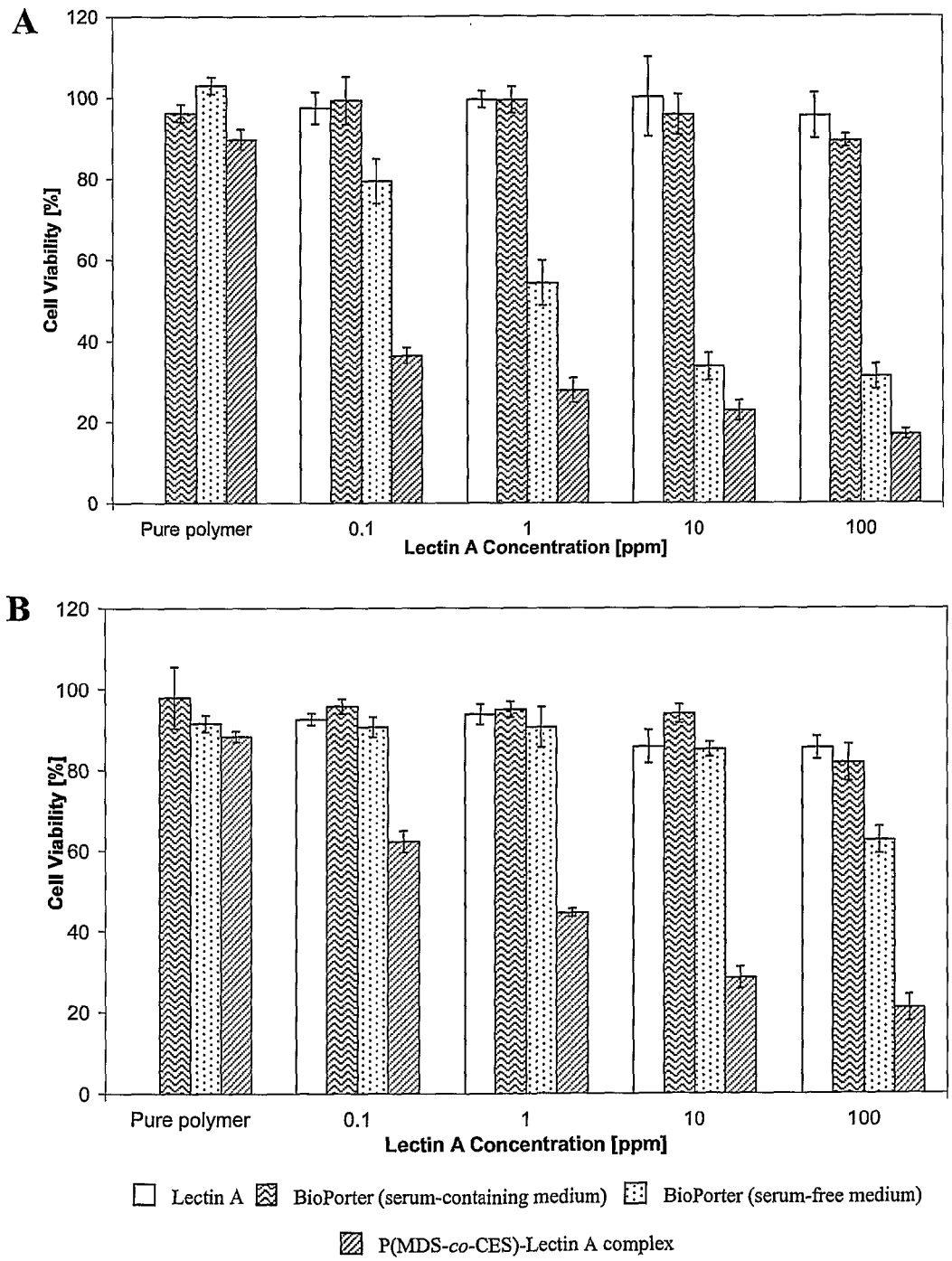
FIG. 4: Comparison studies of P(MDS-co-CES) micelles- and BioPorter-mediated lectin A delivery to MDA-MB-231 (a), HepG2 (b), HeLa (c) and 4T1 (d) cells. P(MDS-co-CES) was used at a fixed concentration of (a) 20 ppm, (b) 50 ppm, (c) 40 ppm and (d) 100 ppm respectively in serum-containing medium. Each condition was tested in eight replicates. The standard deviation is shown by error bars.
Figure 4:
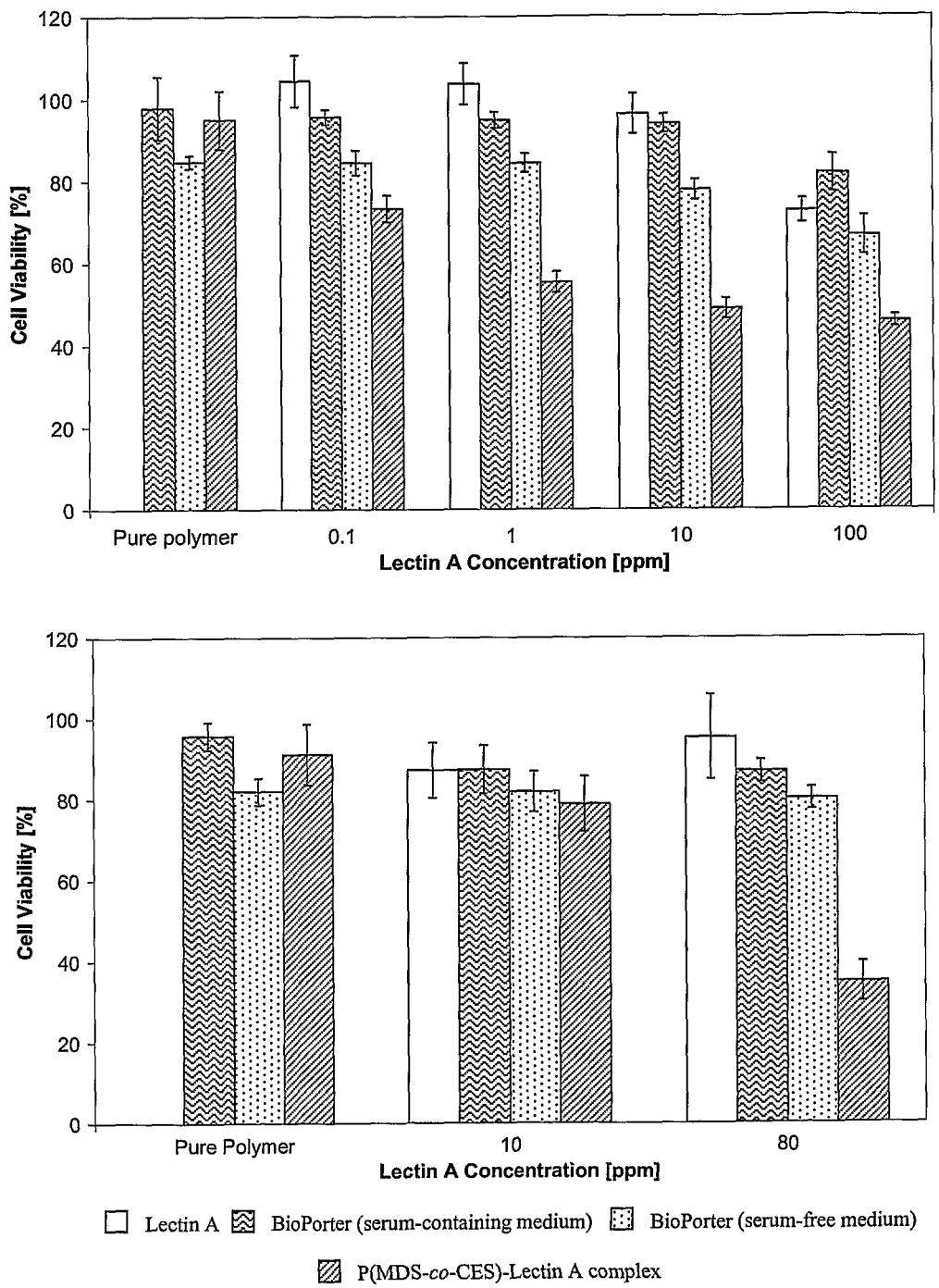

FIG. 4 shows that without the use of the micelles, lectin A did not exhibit significant cytotoxicity especially against MDA-MB-231, HepG2 and 4T1 cells even at 80 to 100 ppm, further proving that lectin A was unable to ender cells by itself. However, the cationic micelles efficiently mediated cellular uptake of lectin A. The cytotoxicity of lectin A using the micelles was compared to that induced by BioPorter. As shown in FIG. 4, in all the four cell lines tested, BioPorter mediated lower cytotoxic effects of lectin A in the serum-containing cell culture medium than in the serum-free medium due to its instability in the presence of serum. However, the cytotoxicity of lectin A induced by micelle/lectin A complexes even in the serum-containing medium was significantly higher than that yielded by BioPorter/lectin A complexes in the serum-free medium. This may be because of greater cellular uptake, stability and endosomal buffering capacity of micelle/lectin A complexes.

These experiments demonstrate that biodegradable and cationic P(MDS-co-CES) micelles can be successfully utilized for intracellular delivery of proteins, as demonstrated here by the delivery of biologically active lectin A to cancer cells. The micelle/lectin A complexes were small enough and of appropriate positive charge distribution for mediating cellular uptake. The micelles also possessed good endosomal buffering capacity to induce intracellular release of lectin A after being taken up by the cells. The cytotoxicity of lectin A delivered by P(MDS-co-CES) micelles was significantly higher even in the serum-containing medium than that induced by BioPorter™. These micelles are thus useful as a carrier for intracellular delivery of proteins, including biologically active proteins and proteins.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

[1] T. J. Yoon, Y. C. Yoo, T. B. Kang, K. Shimazaki, S. K. Song, K. H. Lee, S. H. Kim, C. H. Park, I. Azuma, J. B. Kim, *Cancer Lett.* 1999, 136, 33.
[2] H. S. Lee, Y. S. Kim, S. B. Kim, B. E. Choi, B. H. Woo, K. C. Lee, *Cell. Mol. Life Sci.* 1999, 55, 679.
[3] W. Vervecken, S. Kleff, U. Pfüller, A. Büssing, *Int J Biochem Cell Biol.* 2000, 32, 317.
[4] M. S. Kim, H. S. So, K. M. Lee, J. S. Park, J. H. Lee, S. K. Moon, D. G. Ryu, S. Y. Chung, B. H. Jung, Y. K. Kim, G. Moon, R. Park, *General Pharmacology* 2000, 34, 349.
[5] Y. Endo, K. Tsurugi, H. Franz, *FEBS Lett.* 1988, 231, 378.

[6] O. Zelphati, Y. Wang, S. Kitada, J. C. Reeds, P. L. Felgner, J. Corbeil, *J. Biol. Chem.* 2001, 276, 35103.
[7] O. T. Brustugun, K. E. Fladmark, S. O. Døskeland, S. Orrenius and B. Zhivotovsky, *Cell Death Differ.* 1998, 5, 660.
[8] A. K. Banga, M. R. Praunitz, *Trends Biotechnol.*, 1998, 16, 408.
[9] M. Fenton, N. Bone and A. J. Sinclair, *J. Immunol. Methods.* 1998, 212, 41
[10] K. G. Ford, B. E. Souberbielle, D. Darling, F. Farzaneh, *Gene Therapy* 2001, 8, 1.
[11] J. S. Wadia, S. F. Dowdy, *Curr. Opin. Biotechnol.* 2002, 13, 52.
[12] J. Futami, M. Kitazoe, T. Maeda, E. Nukui, M. Sakaquchi, J. Kosaka, M. Miyazaki, M. Kosaka, H. Tada, M. Seno, J. Sasaki, N. H. Huh, M. Namba, H. Yamada, *J. Biosci. Bioeng.* 2005, 99, 95
[13] Y. Wang, S. Gao. W. H. Ye, H. S. Yoon, Y. Y. Yang, *Nat. Mater.* 2006, 5, 791.
[14] K. C. Wood, S. R. Little, R. Langer, P. T. Hammond, *Angew. Chem. Int. Ed.* 2005, 44, 6704.

What is claimed is:

1. A micelle-protein complex comprising:
a micelle of a cationic polymer, the cationic polymer having a structure of general formula I:

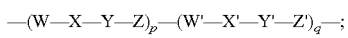

and a protein, the protein having a region available to complex with the micelle;
the protein complexed to the exterior of the micelle via an interaction between the protein and the polymer;
wherein, in general formula I:
each of W, X, Y and Z is independently selected from

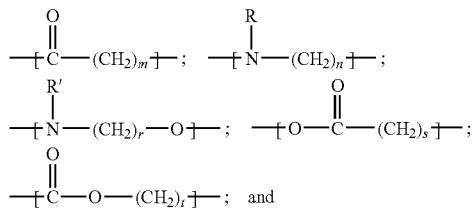

nothing, wherein only one of W, X, Y and Z is nothing and at least one of W, X, Y and Z is a group containing nitrogen bonded to R or R';
each of W', X', Y' and Z' is independently selected from

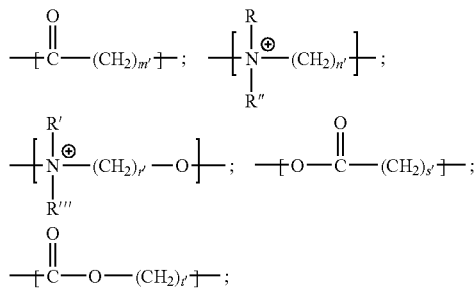

and nothing, wherein only one of W', X', Y' and Z' is nothing, and at least one of W', X', Y' and Z' is a group containing nitrogen bonded to R" or R'";
each of R and R' is independently H, alkyl or heteroalkyl;

each of R" and R'" is independently a hydrophobic group;
each of p and q is independently an integer greater than zero; and
each of m, n, r, s, t, m', n', r', s' and t' is independently an integer greater than 0.

2. The micelle-protein complex according to claim 1, wherein the region of the protein available to complex with the micelle is a negatively charged region.

3. The micelle-protein complex according to claim 1, wherein the cationic polymer comprises poly{N-methyldietheneamine sebacate)-co-[(cholesteryl oxocarbonylamido ethyl)methyl bis(ethylene)ammonium bromide]sebacate}.

4. The micelle-protein complex according to claim 1, wherein the protein is an oligopeptide, a peptide, a polypeptide, a full length protein, a protein fragment, a protein domain, or a fusion protein.

5. The micelle-protein complex according to claim 1, wherein the protein is biologically active.

6. The micelle-protein complex according to claim 5, wherein the protein comprises a hormone, a receptor ligand, a transcription factor, a transcription enhancer, a transcription suppressor, an enzyme, a kinase, a phosphatase, a nuclease, a protease, a growth factor, an antibody, or a cytotoxic protein.

7. The micelle-protein complex according to claim 6 wherein the growth factor comprises Glial-derived neurotropic factor, the cytotoxic protein comprises lectin A, and the antibody comprises herceptin.

8. The micelle-protein complex according to claim 1, further comprising an additional therapeutic agent.

9. The micelle-protein complex according to claim 8, wherein the additional therapeutic agent is a pharmaceutical agent included in the interior of the micelle.

10. The micelle-protein complex according to claim 8, wherein the additional therapeutic agent is a pharmaceutical agent or a nucleic acid molecule complexed to the exterior of the micelle.

11. A method of delivering a protein into a cell comprising:
contacting the micelle-protein complex according to claim 1 with a cell so that the micelle-protein complex is taken up into the cell.

12. The method according to claim 11, wherein the cell is in vitro.

13. The method according to claim 12, wherein the cell is in vivo and the method comprises administering the micelle-protein complex to a subject.

14. The method according to claim 13, wherein the subject is a human.

15. The method according to claim 11, wherein the protein is biologically active and retains biological activity after delivery into the cell.

16. A pharmaceutical composition comprising the micelle-protein complex according to claim 1.

17. The pharmaceutical composition according to claim 16, further comprising a pharmaceutically acceptable carrier.

18. The micelle-protein complex according to claim 4, wherein the protein is biologically active.

19. The micelle-protein complex according to claim 5, further comprising an additional therapeutic agent.

20. The pharmaceutical composition according to claim 16 comprising the micelle-protein complex according to claim 5.

21. The micelle-protein complex according to claim 1, wherein the region of the protein available to complex with the micelle is a polar region.

22. The micelle-protein complex according to claim 1, wherein the region of the protein available to complex with the micelle is a hydrophobic region.

* * * * *